(12) United States Patent
Kristensen et al.

(10) Patent No.: US 7,951,125 B2
(45) Date of Patent: May 31, 2011

(54) SET OF COUPLING PARTS

(75) Inventors: Thomas Kiib Kristensen, Copenhagen (DK); Erik Sorensen, Herlev (DK); Troels Johansen, Nivaa (DK); Lars Olav Schertiger, Fredensborg (DK)

(73) Assignee: Coloplast A/S, Humlebaek (DK)

( * ) Notice: Subject to any disclaimer, the term of this patent is extended or adjusted under 35 U.S.C. 154(b) by 331 days.

(21) Appl. No.: 12/083,596

(22) PCT Filed: Nov. 23, 2006

(86) PCT No.: PCT/DK2006/000654
§ 371 (c)(1),
(2), (4) Date: Apr. 15, 2008

(87) PCT Pub. No.: WO2007/059774
PCT Pub. Date: May 31, 2007

(65) Prior Publication Data
US 2009/0118687 A1    May 7, 2009

(30) Foreign Application Priority Data

Nov. 24, 2005 (DK) ............................ 2005 01652

(51) Int. Cl.
*A61F 5/44* (2006.01)
(52) U.S. Cl. ........ 604/342; 604/332; 604/337; 604/338; 604/339; 604/341; 604/343

(58) Field of Classification Search ................. 604/342, 604/332–341, 343–349
See application file for complete search history.

(56) References Cited

U.S. PATENT DOCUMENTS

| | | | | |
|---|---|---|---|---|
| 5,180,377 A | * | 1/1993 | Holtermann | 604/342 |
| 5,322,522 A | | 6/1994 | Olsen | |
| 5,364,379 A | | 11/1994 | Ozenne et al. | |
| 5,830,200 A | * | 11/1998 | Steer et al. | 604/338 |
| 7,867,207 B2 | * | 1/2011 | Therkelsen et al. | 604/342 |
| 2002/0165507 A1 | * | 11/2002 | Hessel et al. | 604/342 |

FOREIGN PATENT DOCUMENTS

| | | |
|---|---|---|
| EP | 0 381 393 A1 | 8/1990 |
| EP | 0 509 764 A1 | 10/1992 |
| EP | 0 737 456 A2 | 10/1996 |

OTHER PUBLICATIONS

International Preliminary Report on Patentability, PCT/DK2006/000654 (WIPO).*

* cited by examiner

*Primary Examiner* — Melanie J Hand
*Assistant Examiner* — Ginger T Chapman
(74) *Attorney, Agent, or Firm* — Coloplast Corp., Coloplast A/S; Daniel G. Chapik; Nicholas R. Baumann

(57) ABSTRACT

The present invention relates to a set of coupling parts, such as parts for coupling an ostomy bag to a base plate, said base plate being adhered around a stoma. The set of coupling parts provides a connection part that may be interposed between a first coupling part and a second coupling part and where the coupling parts may be connected and disconnected from each other by the same movement of the connection part.

8 Claims, 6 Drawing Sheets

SET OF COUPLING PARTS

This is a national stage of PCT/DK2006/000654 filed on Nov. 23, 2006 and published in English.

FIELD OF THE INVENTION

The present invention relates to a set of coupling parts, such as parts for coupling an ostomy bag to a base plate, said base plate being adhered around a stoma.

BACKGROUND

Ostomy coupling arrangements are used to connect so called two-piece ostomy bags. Theses two-piece ostomy bags comprises an ostomy bag for receiving stomal discharge, the ostomy bag have a coupling part which is adapted to couple with a coupling part on a base plate which is adhered to the skin of the user in an area around the stoma.

In this way the ostomy bag can be changed after use without having to change the base plate each time.

Many different types of coupling arrangements for securing an ostomy bag to a base plate are known all trying to fulfill different demands for the coupling between the base plate and the ostomy bag. Such demands are for example that the couplings are tight and secure so that no stoma discharge is leaked, that the coupling is discreet so that the ostomy bag can be carried beneath ordinary clothes and that the coupling is easy to operate.

In EP 0 509 764 B1 a two-piece ostomy bag is proposed having a coupling for joining a pad or dressing to the ostomy bag including a first member of closed loop form for defining a stoma aperture therein. The first member has a formation, which defines two opposed walls. A second member of closed loop form also defines a stoma aperture and the second member have a projection dimensioned and positioned to fit with and resiliently bear against at least one of the walls when the members are connected.

U.S. Pat. No. 5,364,379 proposes stoma equipment comprising a bag-carrier for fixing around an artificial opening in the body of a user by means of a base plate provided with an adhesive or with a pressure-sensitive adhesive rubber or with any equivalent means, together with a bag for collecting body wastes and/or fluids and suitable for being removably assembled to a sleeve or collar of the bag carrier by means of a rim on the bag, wherein the bag is fixed on the bag-carrier by deforming sealing means whose radial size is increased by operating an appropriate actuator device.

EP 0 737 456 B1 discloses an ostomy coupling having first and second coupling members. The members are held together by a springy flexible split locking ring. A plurality of tabs, arranged, e.g. symmetrically, on the limbs of the locking ring, can be withdrawn generally radially outwardly by movement of the locking ring to permit separation of the two coupling members. The movement of the locking ring, which causes withdrawal of the tabs, is a rotational movement relative to the second coupling member.

SUMMARY

Among others it is an aspect of the present invention to provide an improved set of ostomy coupling parts that are safe to wear and do not accidentally uncouple.

Another aspect according to the invention is a set of ostomy coupling parts that are easy to couple and uncouple.

Another aspect according to the invention is a set of ostomy coupling parts that are discrete and comfortable to wear.

Another aspect according to the invention is a set of ostomy coupling parts that provides a tight and secure seal.

Accordingly the present invention discloses a set of coupling parts for detachably connecting a first member and a second member by moving the second member axially in a connecting direction towards the first member, the set of coupling parts comprising; a first coupling part arranged on the first member, the first coupling part comprising a first base and a first wall extending axially from the first base, and a first stop extending radially outwardly from the first wall towards a first free end of the first stop; a second coupling part arranged on the second member, the second coupling part comprising a second base and a second wall extending axially from the second base, and a second stop extending radially inwardly from the second wall towards a second free end of the second stop; a connection part comprising an inner surface facing inwards towards the axis and an outer surface facing outwards away from the axis, and that the set of coupling parts, when arranged along an axis parallel to the connection direction, in at least one area further comprises; a first radius of the first free end is smaller than a second radius of the second free end; the outer surface is movable between a third radius of the outer surface, which is larger than the second radius, and a fourth radius of the outer surface, which is smaller than the second radius; the outer surface is biased towards the third radius; and a fifth radius of the inner surface is smaller than the first distance.

This advantageously provides a set of coupling parts wherein the connection part may be interposed between the first coupling part and the second coupling part and where the coupling parts may be connected and disconnected from each other by the same movement of the connection part.

It should be understood that when connected the first member in the second member are moved relative to each other. However, in the following description the connecting direction should be understood as being the direction of the second member is moved in order to connect it to the first member. The connection will at least partly comprise movement along the axis, for example when the second coupling part is coupled at an angle to the axis.

The set of coupling parts may be formed of a number of different materials. When used to connect ostomy bags and base plates the set of coupling parts are often formed of polymers. When the set of coupling parts are formed of such polymers, they are often flexible in different direction. Such flexibility may result in that the different coupling parts are bent or deformed to different shapes in different areas along the different parts. Thus, in order to describe the parts a cross section there through is considered. The cross section shows at least one area where the set of coupling parts are arranged along an axis parallel to the connection direction. In case each of the coupling parts bends or otherwise forms equally along the entire part the at least one area will correspond to any random sectional area considered along the axis. Some materials, such as the mentioned polymers, may show different properties in different areas.

In order for the outer surface to be movable between a third radius and a fourth radius the connection part may be formed as an open ring. By open ring it should be understood that the ring is open in one area, thereby providing two ends. The ends may be moved towards or/and away from each other, whereby different radiuses of the open ring may be provided.

It should be understood that in the present context the use of the term radius, e.g. the first, second, third, fourth and fifth radius mentioned above, should not necessarily be read as absolute values. Rather each radius may be able to have different values within an interval depending on different embodiments. The radiuses should be understood as being an arbitrary value that fulfils the relations between the different radiuses as described herein.

In one embodiment the set of coupling parts comprises a bevel surface axially extending between the outer surface and a proximal edge of the bevel surface. The bevel surface forms an angle of more than zero and less than ninety degrees to the outer surface.

This provides for a smooth transition when the connection part is assembled with the first coupling part. Furthermore, by providing a sixth radius of the proximal edge of the bevel surface which is smaller than the second radius the beveled surface will function as a guide surface for the second stop as the second part is connected with the connection part.

In another embodiment the first coupling part and the connection part is arranged in an assembled configuration wherein the connection part extends axially between the first base and the first stop. Advantageously the distance between the first base and the first stop is slightly larger than the axially extending distance of the connecting part, thus some clearance will be provided allowing the connecting part to be freely operable.

Furthermore an inner flange may be provided which extends radially outwardly from the first base and thereby defines a groove together with the first stop and first wall. The connection part may advantageously be received in said groove.

In a preferred embodiment the groove is U-shaped, however, it will be understood by the person skilled in the art that the groove may have many different shapes, such as for example V-shaped.

The second coupling part may be connected to the connecting part in different ways. For example this may be done by providing a second outer surface on the connection part upstream of the first outer surface when seen in the connecting direction, and where a seventh radius of the second outer surface is smaller than the third radius. Thus a cut is provided on the connecting part wherein at least a part of the second stop can be received.

Alternatively the second coupling part and the connection part may be connected by a frictional connection. This may for example be realized when the seventh radius is larger than the second radius whereby the second outer surface will press against the second free end when the set of coupling parts are coupled.

Due to production tolerances or design there may be some radial clearance between the connection part and the first wall of the first coupling part. The connection part will thereby typically be placed in a position eccentric from the first coupling part. Thus, in order to position the connection in concentric relation with the first coupling part biasing means being radially flexible may be provided between the connecting part and the first wall.

Thus the connecting part will always be placed in the same position relative to the first coupling part which is an advantage to the user, as they do not always look at the set of coupling parts but often just connect the parts by habit and experience and therefore relies on that the parts are arranged almost identical each time.

Such biasing means may for example be provided by flat springs, which at least extend partially in a radial direction. Alternatively an elastic material may be provided between the connecting part and the first, such as rubber or foam. Furthermore the biasing means may be provided on the connection part or the first wall extending towards the opposite part, or alternatively the biasing means may be provided on both parts.

In one embodiment the second coupling part may comprise a third wall extending radially from the second base. The second wall, the base and the third wall may thereby define a first recess. The axial extent of the first recess is advantageously equal to or larger than the axial extent of the first stop. Thus the recess may function as receiving means wherein the at least the first stop may be received when the set of coupling parts are connected providing a stable connection while also aiding in placing the parts correctly relative to each other.

Alternatively or additionally the third wall may be radially flexible. This provides sealing means, which may abut against the first wall preventing liquid to leak out between the first and the third wall.

In order to easily get hold of the second coupling part, for example when pulling it off after use the second coupling part may further comprises a flap extending radially outwardly from the second wall. The flap will typically be large enough for a person to grab it between two fingers.

As can be understood the set of coupling part may be used for many different applications where a first member and a second member is to be connected. In one embodiment the first coupling part is attached to an adhesive base plate and the second coupling part is attached to the ostomy bag.

Furthermore, different additional components may be added to the assembly when the sets of coupling parts are attached to a base plate and an ostomy bag. Such additional components are well known in the art and may be added depending on the product line and the target group for the specific ostomy product. In order for the user to secure the construction to a belt, belt ears in the shape of for example loops or hooks may be added to the first coupling part, or the base plate.

A so-called convex element may additionally or alternatively be used with the base plate and the first coupling part in order to give the base plate a convex shape in an area in order to shape the construction to certain types of retracted ostomies for higher comfort and reduced risk of leakage.

When the connection part is moved to its third radius it can be said to be in a coupling configuration where it will be ready to couple, or already coupled with the second coupling part. Vice versa the connection part can be said to be in an uncoupling configuration when the connection part is moved to its fourth radius.

The connection part can advantageously comprise locking means for in an unloaded state keeping the connection part in its coupling configuration. This prevents the connection part from unintentionally falling of and/or always being ready to couple with the first and second coupling parts.

It should be understood that such locking means do not hold the connection part in a fixed configuration but that the connection part still may be movable between its coupling and uncoupling configuration while the locking means are engaged.

In one embodiment the connection part may as mentioned earlier be formed as an open ring. The locking means may for example be provided by a key provided at one end of the open ring and a slot provided at a second end of the open ring, wherein the key is able to engage with the slot. The slot preferably has an elongated shape wherein the key can slide between different positions, moving the connecting part between the third radius and the fourth radius.

The open ring may additionally be provided with a hinge dividing the ring in to sections. By dividing the ring by a hinge the deformation will occur around the rotational axis of the hinge instead of through the entire connection part.

Spring means are provided between the two open ends whereby the ring will be deformed, i.e. moved from the third radius to the fourth radius, when the ends are pressed together and the spring will return the connection part to an original position when the pressure is removed.

A bridge of flexible material, such as a polymer film, can be provided between the two ends thereby connecting them. This will advantageously prevent the two ends to be separated more than the length of the bridge. Thus the maximal deformation of the coupling part can controlled and the coupling part can thereby be formed to fit between the first base and the first stop.

The set of coupling part can be produced of many different types of material, but will typically be formed of different types of plastics, which can be used for injection moulding.

When used as a set of coupling parts for coupling an ostomy bag to a base plate, the set of coupling parts can be formed of material as suggested below.

The connection part can for example be made from POM (polyoxymethylen), ABS (acryinitril-butadien-styren-co-polymer) or PP (polypropylen). These materials all have suitable flexible properties.

The first coupling part, when used as part of the base plate, can for example be formed of LPDE (low density polyethylen) or LLPDE (linear low density polyethylen).

The second coupling part, when used as a part of the ostomy bag, can for example also be formed of LPDE or LLPDE. Alternatively it can be formed of two materials, i.e. two component, such as PP (polypropylen) and EVA (ethylene-vinyl-acetate); or ABS (acryinitril-butadien-styren-co-polymer)/TPE (thermo-plastic-elastomers). By forming the coupling part of two materials it is possible to provide the part with different characteristics in different areas.

FIGURES

DETAILED DISCLOSURE

Figure 1:
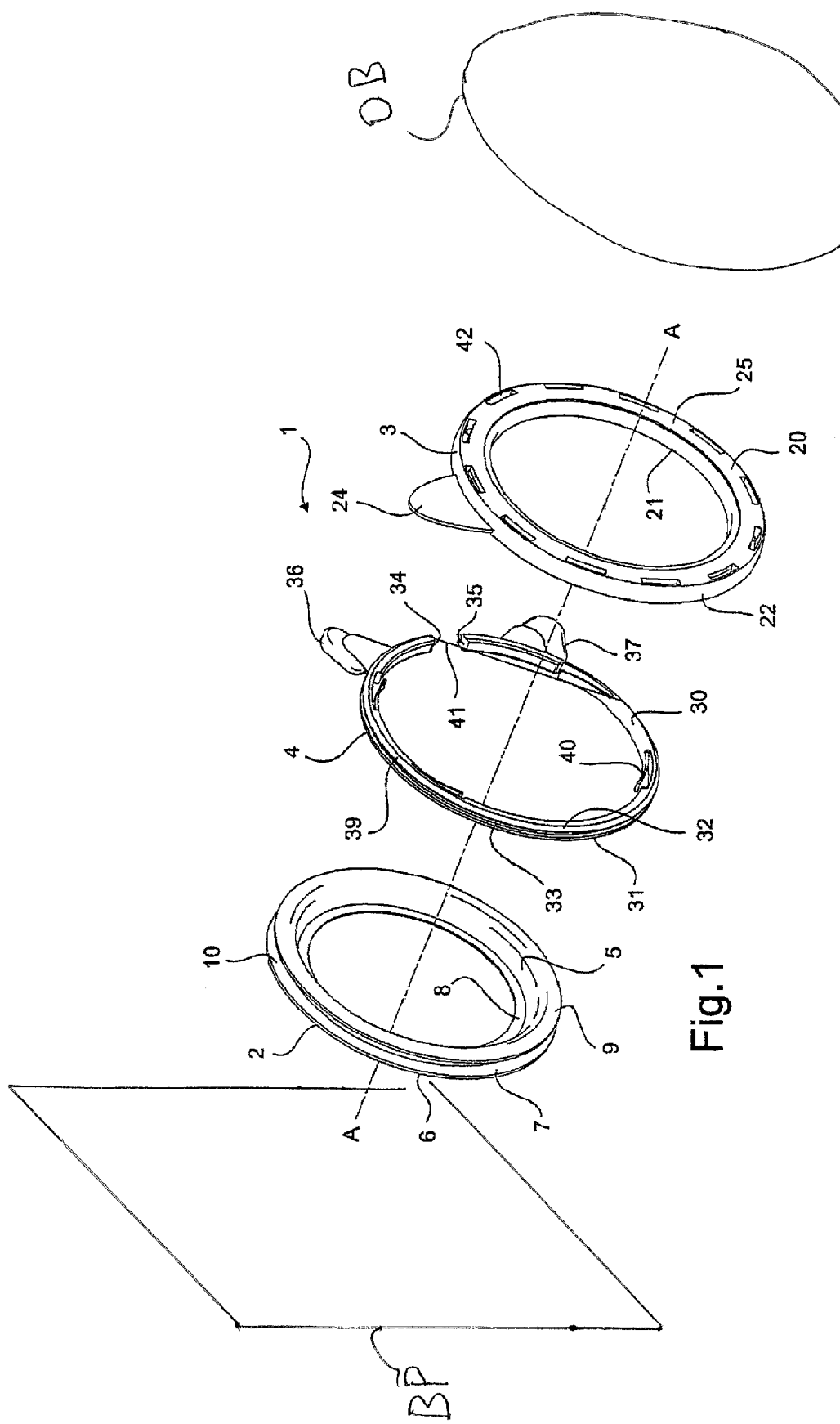
FIG. 1 shows in a perspective and exploded view one embodiment of the set of coupling parts according to the invention.
Figure 2:
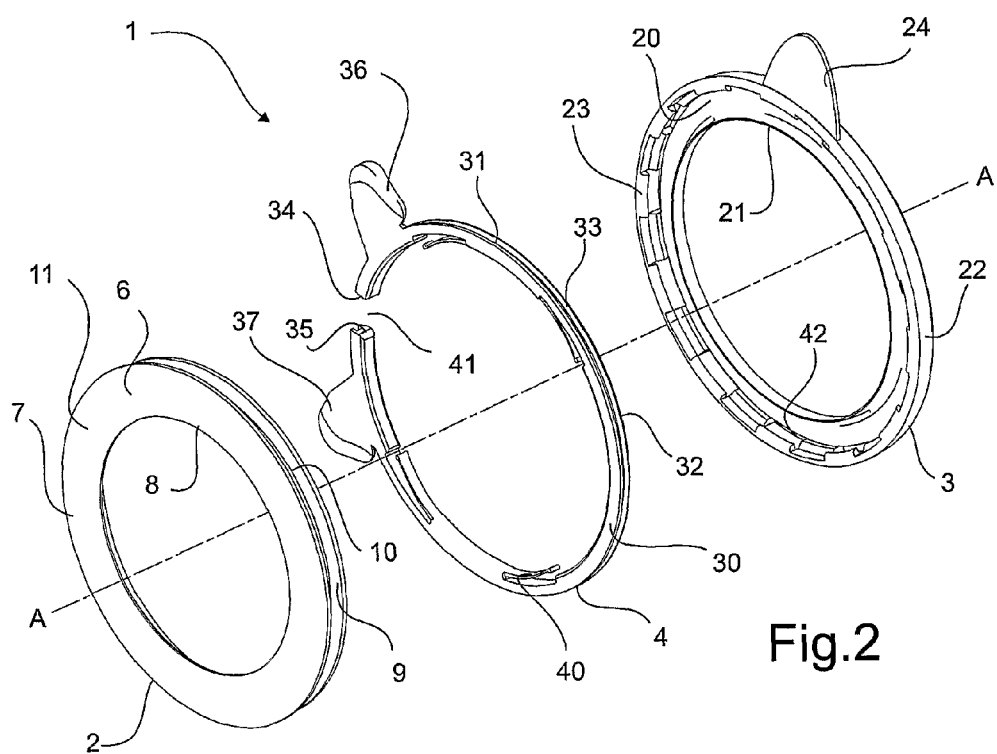
FIG. 2 shows in a perspective and exploded view the one embodiment of the set of coupling parts in FIG. 1 from another view.
Figure 4:
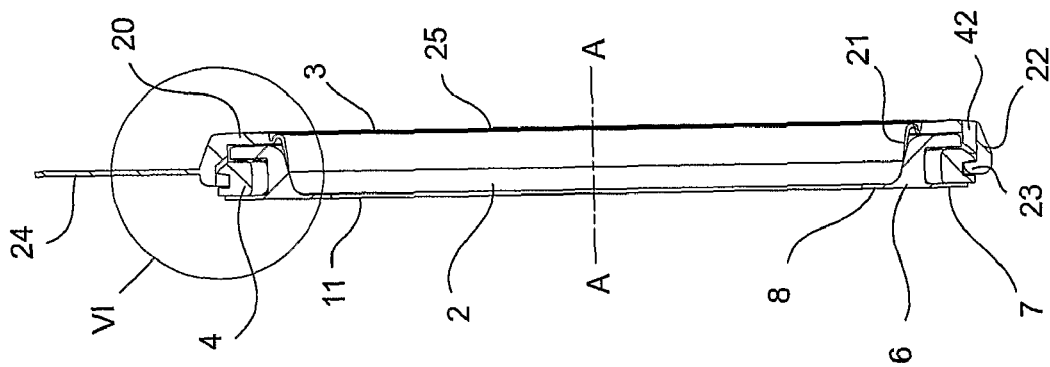
FIG. 4 shows in cross-section above embodiment along lines IV-IV in FIG. 3, FIGS. 5, 6 and 7 show seen in section the embodiment illustrated in FIG. 1 in different positions.
Figure 3:
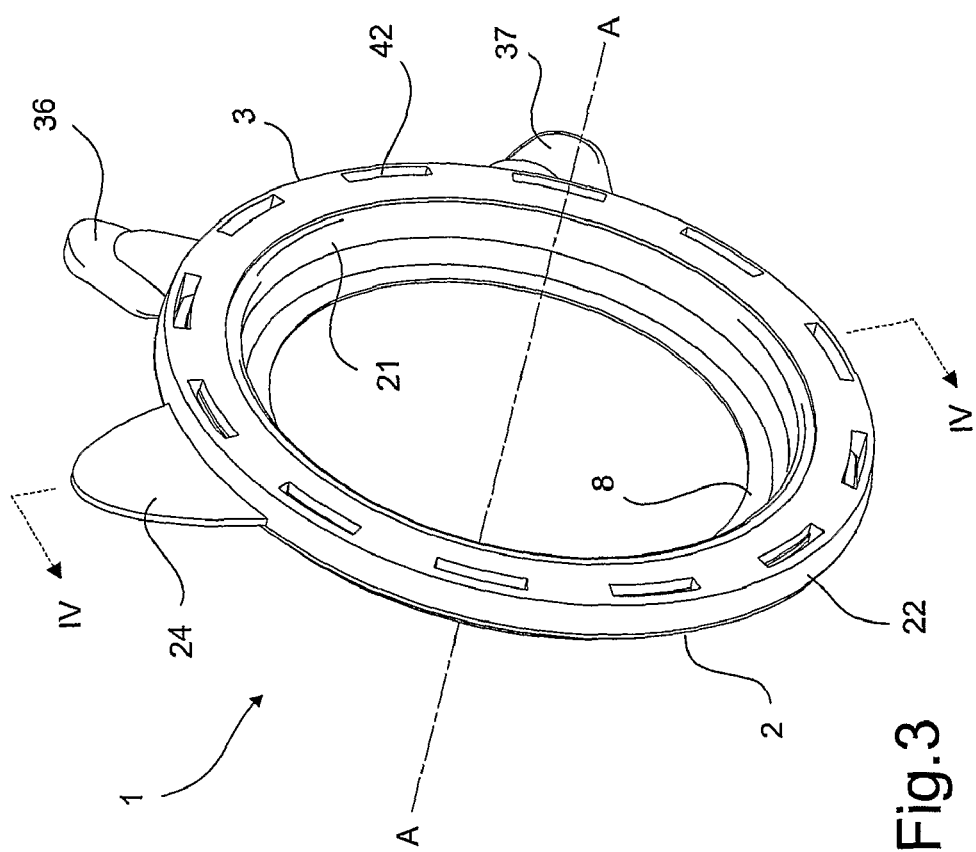
FIG. 3 shows in a perspective view the embodiment shown in FIG. 1 in a coupling position.
Figure 5A:
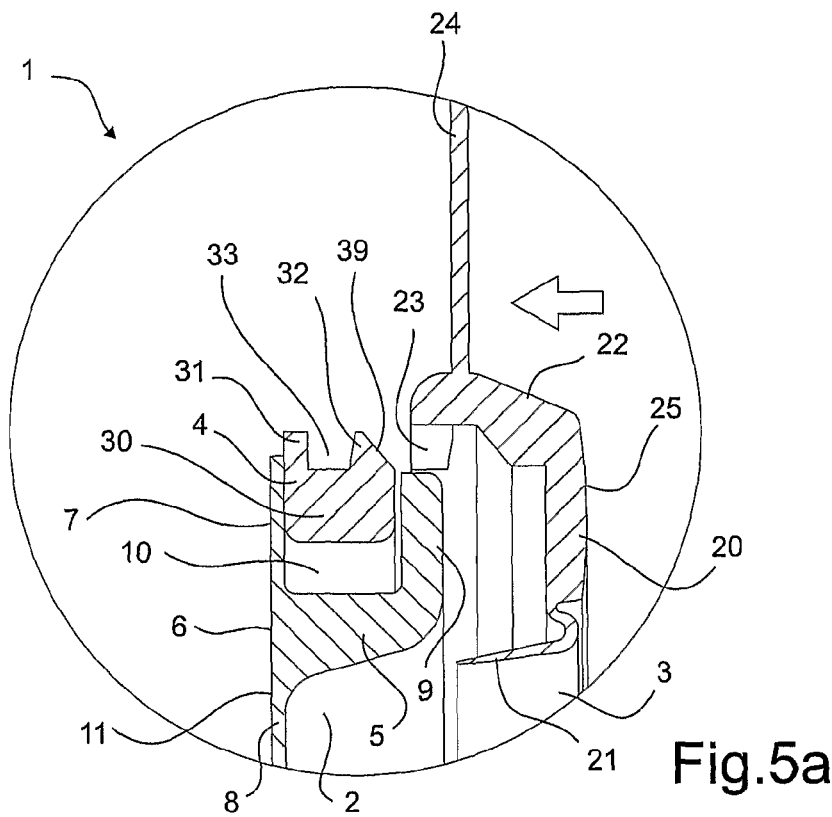
Figure 5B:
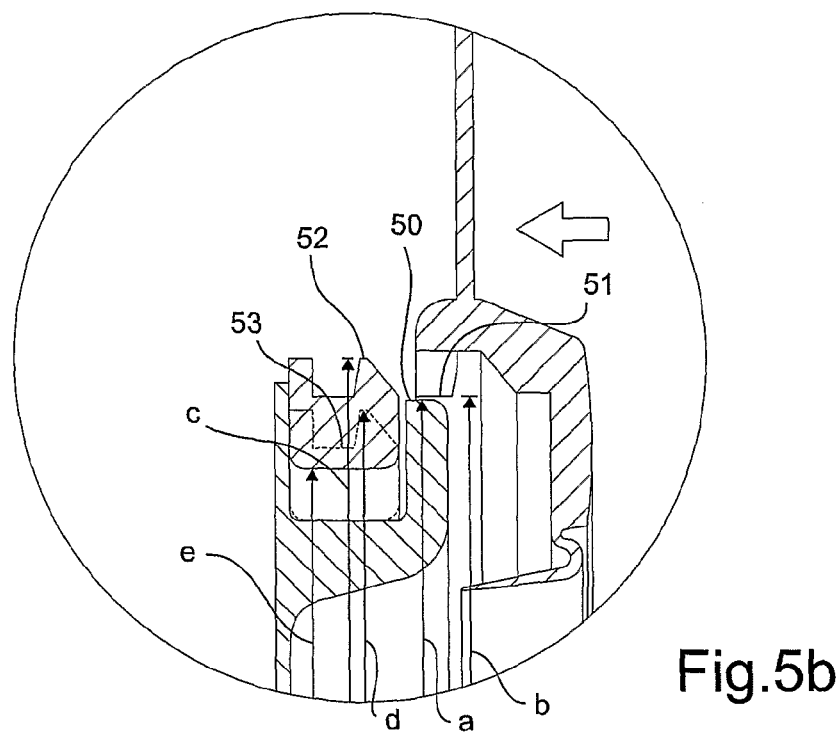
Figure 6:
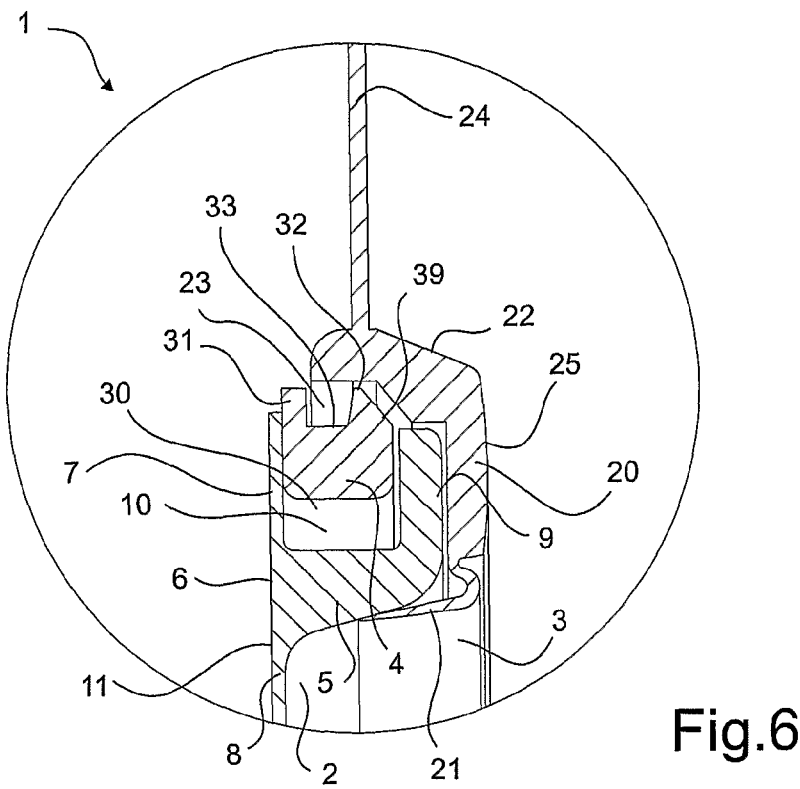
Figure 7:
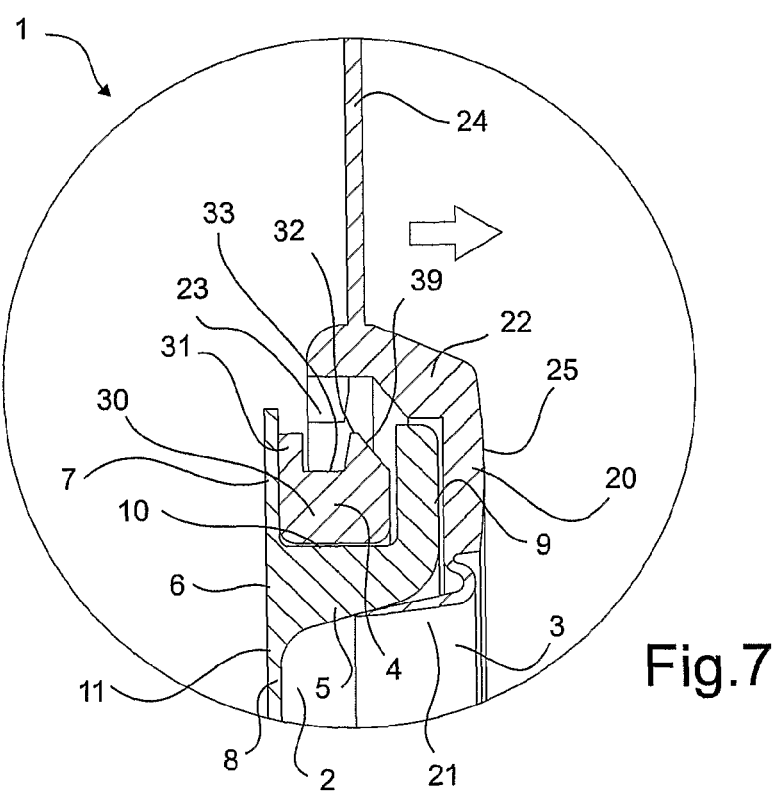

FIGS. 1-7 shows a first embodiment of a set of coupling parts 1 according to the invention shown in different views and sections. FIGS. 1 and 2 shows the set of coupling parts from two different perspective angles in exploded view along the axis A-A. FIG. 3 shows the set of coupling parts in an perspective view where the parts are coupled together. FIG. 4 shows in cross section the set of coupling parts along the line IV-IV in FIG. 3. FIGS. 5a, 5b, 6 and 7 shows seen in section a part of the set of coupling parts in different positions during coupling and uncoupling wherein FIG. 6 is an enlargement of section VI in FIG. 4. FIG. 5b is an additional view of FIG. 5a in order to keep the illustrations simple and clear.

The set of coupling parts 1 consists of a first coupling part 2, a second coupling part 3 and a connection part 4. The first coupling part is adapted to be attached to a base plate BP and the second coupling part is adapted to be attached to an ostomy bag OB. Thus, when coupled the set of coupling parts will couple the base plate BP and ostomy bag OB together, and the set of coupling parts will thus be arranged between the base plate and the bag.

In the following it should be understood that each part of the set of coupling parts can be viewed as being divided into a number of different elements as will be understood in the following. The elements have an axial extent, which extends along the axis A-A. The axial extent is defined by a proximal surface of the element and a distal surface of the element. The proximal surface of the element is the surface that faces the base plate and the distal surface of the element is the surface that faces the ostomy bag.

Furthermore, the elements also have a radial extent, being an extent transverse to the axis A-A, defined as being between an inner surface of the element and an outer surface of the element. The inner surface faces inwards towards the axis A-A and the outer surface faces outwards away from the axis A-A.

The first coupling part 2 has an annular wall 5 extending axially from a first annular base 6. A first proximal flange 7 extends radially outwards from the first base 6 and a second proximal flange 8 extending radially inwards from the first base 6. At the distal end of the annular wall there is formed a distal flange 9, which extends radially outwards from the annular wall.

The annular wall 5, the first proximal flange 7 and the distal flange 9 define a first U-shaped groove 10. The opening of the groove faces radially outwardly.

The first base 6, the first proximal flange 7 and the second proximal flange 8 has a common proximal surface 11, which is attachable to an adhesive base plate (not shown).

Attachment may be done by welding or gluing at least a part of the proximal surface to the base plate.

The second coupling part 3 has a second annular base 20 extending radially between an inner wall 21 and an outer wall 22. The second outer wall extends axially between the second base 20 and a set of radially inwardly extending tabs 23.

The tabs 23 are equidistantly placed, describing a circle. Through going holes 42 are formed in the second base 20. The placement of the holes corresponds to the placement of the tabs. This construction is formed during molding and is provided because the mold comprises two parts which needs to be separable in one direction. Other techniques to mold the set of coupling parts, for example to provide a continuous annular tab, can be provided by the person skilled in the art. Such techniques are not an issue or a limitation of the present invention and will therefore not be further discussed.

A flap 24 is provided on the second coupling part and extends radially outwards from an area on the outer wall 22.

The second base 20 has a distal surface 25 which is adapted to be attached to an ostomy bag (not shown). Attachment may be done by welding or gluing at least a part of the distal surface to the ostomy bag.

The connection part is formed as a ring 4, having an annular ring base 30, a first ring rim 31 extending radially outwards from the ring base and a second ring rim 32 extending radially outwards from the ring base. The outer surface of the ring base, the distal surface of the first ring rim and the proximal surface of the second ring rim define a second U-shaped groove 33. The opening of the second groove faces radially outwards.

In an alternative embodiment (not shown), the first ring rim is removed. Thus, when the ring is placed in the first groove the second ring rim and the first proximal flange of the first coupling part define the U-shaped groove.

The ring is interrupted in one area, resulting in a gap 41, defining a first end 34 and a second end 35. A first grip 36 is arranged close to the first end 34 and a second grip 37 is arranged close to the second end 35.

A beveled surface 39 is formed on the distal side of the second ring rim. The beveled surface forms an angle of approximately forty-five degrees to the axis A-A.

Four flexible springs 40 extending inwardly from the inner surface of the ring in a partly helical path providing radially flexible means.

In a modified embodiment (not shown) the four flexible springs are formed in the first groove of the first coupling part extending outwardly from the first groove in a partly helical path, thereby providing the radially flexible means.

The separate parts are typically manufactured in individual molds. The proximal surface 11 of the first coupling part is then attached to a base plate (not shown) and the distal surface 25 of the second coupling part is attached to the ostomy bag (not shown). The ring is then placed in the first groove 10. In order for the ring to fit into the first groove the axial extent of the ring base is slightly less than the distance between the distal surface of the first ring rim and the proximal surface of the second ring rim.

The ends of the flexible springs 40 describe an enveloping circle having a circumference which is slightly less than the circumference of the outer surface of the first annular wall 5. This allows for the ring to be placed in a suspended position where the springs abut against the outer surface of the annular wall. The ring will thereby position itself evenly in the first groove.

When the set of coupling parts is to be connected, as shown in FIGS. 5a and 5b, the second coupling part is moved relative to the first coupling part and the ring in an axial direction as indicated by the open arrow.

The edge defined by the proximal surface and the inner surface of tabs 23 will abut against the beveled surface 39. Due to the clearance between the outer surface of the annular wall 5 and the inner surface of the ring base 30 and the gap 41 the ring is allowed to be compressed allowing the tab to move along the beveled surface 39. By compressed it should be understood that the inner circumference of the ring 4, i.e. a continuous curve defined by the inner surface of the ring base and an imaginary extension of the inner surface bridging the gap 41, is decreased while the tabs slide along the beveled surface 39.

The inner surface of the tabs 23 will subsequently slide along the outer surface of the second ring rim 32 and as the edge defined by the inner surface of the tabs 23 and the distal surface of the tabs 23 passes the proximal surface of the second ring rim 32 the ring will expand and the tabs 23 will be received in the groove the 33.

In order for the ring to expand it will typically be formed of a flexible material as described earlier. When manufactured the ring is molded in its expanded position whereby the properties of the material will provide the biasing characteristic of the ring.

Thus, when coupled the set of coupling parts are arranged in their coupled configuration as shown in FIG. 6. As can be seen the second ring rim acts as a stop against the tab 23 preventing the set of coupling parts to uncouple from each other.

Furthermore, when in the coupled configuration the inner wall 21 of the second coupling abuts against the inner surface of the annular wall 5. The inner wall is slightly flexible allowing it to follow the curvature of the annular wall. This provides sealing between the first coupling part and the second coupling part preventing odor and discharge from a stoma to leak through the set of coupling parts and into the outside environment.

When the set of parts are uncoupled the first grip 36 and second grip 37 are manually pressed towards each other thereby compressing the ring and decreasing the inner circumference of the ring. The ring is compressed until the distance from the axis A-A to the outer surface of the second ring rim is smaller than the distance from the axis A-A to the inner surface of the tab in at least one area of the set of coupling parts. The second coupling part can the be uncoupled by pulling it in an axial direction away from the first coupling part and the ring as indicated by the open arrow in FIG. 7.

One advantage of the first illustrated embodiment is that the ring typically is compressed into an oval shape when the first and second ends are pressed towards each other. This results in that the coupling parts in the main are uncoupled except at an area approximately opposite the handles. Thus, the second coupling parts will not accidentally fall off but the user will have to apply a small tug to properly separate the second coupling part from the ring.

To ease uncoupling the user can pull the flap 24, which is large enough to grip between two fingers.

FIG. 4 shows the section IV-IV in FIG. 3. The section VI in FIG. 4 is shown in enlarged view in FIG. 6 and FIGS. 5a and 5b shows the set of coupling parts according to the invention in the same sectional view as in FIG. 6 but where the second coupling is disconnected from the first coupling part and the connection part. Thus it can be understood that FIGS. 5a and 5b shows at least one are where the set of coupling parts are arranged in along an axis A-A parallel to the connection direction.

As can be seen in the embodiment illustrated in FIG. 5b different distances to the axis A-A may be considered in order to provide a set of coupling parts according to the invention.

A first radius, a, between the axis A-A and a first free end 50, i.e. the outer surface of the distal flange 9, is smaller than a second radius, b, between the axis A-A and a second free end 51, i.e. the inner surface of the tabs 23. This allows the tabs to pass the distal flange when connecting and disconnecting the second coupling from the first coupling part and the connecting part.

The first outer surface 52, i.e. the outer surface of the second ring rim, is movable between a third radius, c, between the axis A-A and the first outer surface, which is larger than the second radius, b, and a fourth radius, d, between the axis A-A of the first outer surface, which is smaller than the second radius. The broken line 53 indicates the position where the second ring rim has its fourth radius. This allows for the second ring rim to prevent the tabs 23 engaged in the groove 33 to be pulled out from the groove when the first outer surface is moved to its third radius. The second coupling part is however easily disconnected from the connection part when the first outer surface is moved to its fourth radius.

The connection part 4 is formed of an elastic polymer and when moulded the first outer surface is formed when the first outer surface has its third radius. Thus, the first outer surface will be biased towards the third radius. This provides simple coupling engagement between the connection part and the second coupling part whereby no additional means are required to keep the first outer surface in a position wherein it has its third radius.

In order to keep the connection part assembled with the first coupling part the connection part has a fifth radius, e, between the axis A-A and a first inner surface, i.e. the inner surface of the inner surface of the ring base 30, is smaller than the first distance, a. Thus, even though the connection part is moved between the third and fourth radius the fifth radius will in both positions be smaller than the first distance and thereby not be removed from the first coupling part.

Figure 8:
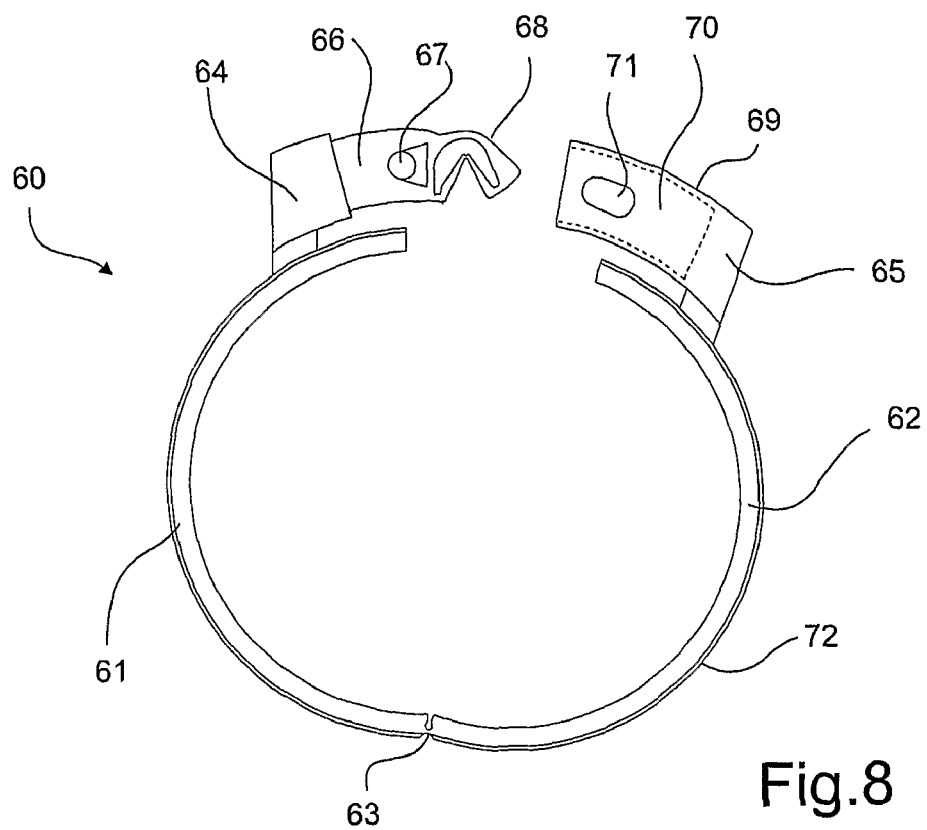
FIGS. 8 and 9 shows a second embodiment of the connection part.
Figure 9:
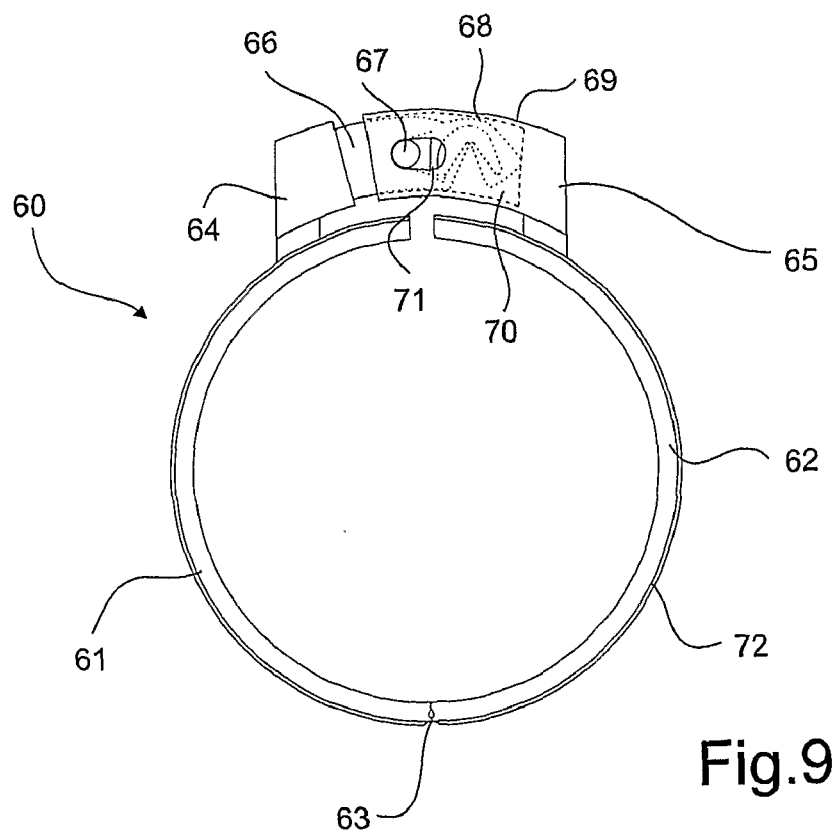

An alternative embodiment 60 of a connection part is shown in FIGS. 8 and 9. A first 61 and a second half circle 62 joined by a hinge 63 form a second connection part 60.

At their free ends the first and second half circle are provided with a respective first grip and second grip 64,65.

A first tab 66 extends from the first grip. The first tab is provided with a key 67, which extends in the axial direction. Opposite the first grip 64 the first tab is provided with a spring element 68, which is flexible in the direction of which the first and second grip is pressed towards each other, i.e. in a direction corresponding to rotation around the hinge 63.

A second tab 69 extends from the second grip 65 towards the first tab. The second tab is formed with a groove 70, indicated by broken lines, for receiving the first tab 66. A slot 71 is formed on the second tab for receiving the key 67.

The second connection part 60 can for example be use with the first and second coupling part 2,3 described in FIG. 1-7, instead of the connection part 4. The second connection part can be placed in the first groove 10, whereby it is closed so that the key 67 is received in the slot 71 as shown in FIG. 9. The second coupling can then be coupled with the first coupling part by pressing it onto the second connection part whereby the tabs 23 will click into a groove defined by a recess 72 on the second connection part 60 and the first coupling part 2.

When the key 67 is engaged with the slot 71 the second connection part 60 is in its coupling configuration and is ready to be or already coupled with the second coupling part, the spring element 68 will abut against the side of the grip 65, thereby biasing the second connection part into its coupling configuration. When the second coupling part 3 is to be uncoupled the first and second grip 64,65 is pressed towards each other thereby decreasing the circumference of the second connection part 60 and releasing the second coupling part 3. As the pressure on the first and second grip is released the spring element will cause the second connection part to return to its coupling configuration as shown in FIG. 9.

It should be understood that the described embodiments are exemplary only and that a number of modifications and alternative embodiments may be provided within the scope of the invention.

Thus, for example, the present invention is not limited too that the coupling parts and the locking ring are circular, but may shaped in many different geometrical shapes such as ellipsoids, squares, trapezoids, polygons etc.

REFERENCE NUMBERS 1. set of coupling parts
2. first coupling part
3. second coupling part
4. connection part
5. annular wall
6. proximal annular base
7. first proximal flange
8. second proximal flange
9. distal flange
10. first groove
11. proximal surface
20. distal annular base
21. inner wall
22. outer wall
23. tabs
24. flap
25. distal surface
30. annular ring base
31. first ring rim
32. second ring rim
33. second groove
34. first end
35. second end
36. first grip
37. second grip
39. beveled surface
40. flexible springs
41. gap
50. first free end
51. second free end
52. first outer surface
53. broken line
60. alternative embodiment
61. first half circle
62. second half circle
63. hinge
64. first grip
65. second grip
66. first tab
67. key
68. spring element
69. second tab
70. groove
71. slot
72. recess

The invention claimed is:

1. A set of coupling parts for detachably connecting a first member and a second member by moving the second member axially in a connecting direction towards the first member, the set of coupling parts comprising,
   a first coupling part arranged on the first member, the first coupling part defining a first groove formed between a promixal wall and a distal wall,
   a second coupling part arranged on the second member, the second coupling part comprising a base and an inner wall and outer wall each extending axially from the base to define a recess that is sized to receive the distal wall of the first coupling part, the second coupling part including a tab extending radially inwardly from the outer wall,
   a connection part comprising an inner surface facing inwards towards the axis and an outer surface facing outwards away from the axis and defining a radial groove formed in a periphery of outer surface;
   wherein the connection part is insertable into the first groove of the first coupling part and the tab of the second coupling part is insertable into the radial groove of the connection part to retain the first coupling part and the connection part within the recess of the second coupling part.

2. A set of coupling parts according to claim 1, wherein the connection part comprises a bevel formed on the distal side that extends between the radial groove and a portion of the outer surface.

3. A set of coupling parts according to claim 1, wherein the first coupling part and the connection part provide an assembled configuration wherein the connection part extends axially between the proximal wall and the distal wall of the first coupling part.

4. A set of coupling parts according to claim 1, wherein the connecting part comprises radially flexible biasing means.

5. A set of coupling parts according to claim 1, wherein the second coupling part further comprises a flap that extends radially outward from the outer wall.

6. A set of coupling parts according to claim 5, wherein the flap is configured to disengage the tab of the second coupling part from the radial groove of the connection part.

7. A set of coupling parts according to claim 1, wherein the first coupling part is attached to an adhesive base plate and the second coupling part is attached to an ostomy bag.

8. A set of coupling parts according to claim 1, wherein the connection part is formed as an open ring having,
 a key provided at one end of the open ring,
 and a slot provided at a second end of the open ring, and that
 the key is able to be received in the slot.

* * * * *